United States Patent
Cotter et al.

(10) Patent No.: US 11,284,915 B2
(45) Date of Patent: Mar. 29, 2022

(54) ULTRASONIC SURGICAL HANDPIECE HAVING A THERMAL DIFFUSER

(71) Applicant: Integra LifeSciences Enterprises, LLLP, Princeton, NJ (US)

(72) Inventors: Daniel J. Cotter, North Easton, MA (US); Prakash Manandhar, Lawrence, MA (US); Igor V. Kosenko, Boxborough, MA (US); Saurav V. Gupta, Medway, MA (US)

(73) Assignee: Integra LifeSciences Enterprises, LLLP, Princeton, NJ (US)

( * ) Notice: Subject to any disclaimer, the term of this patent is extended or adjusted under 35 U.S.C. 154(b) by 695 days.

(21) Appl. No.: 15/813,899

(22) Filed: Nov. 15, 2017

(65) Prior Publication Data

US 2018/0132885 A1   May 17, 2018

Related U.S. Application Data

(60) Provisional application No. 62/422,635, filed on Nov. 16, 2016.

(51) Int. Cl.
*A61B 17/32* (2006.01)
*B06B 1/06* (2006.01)
(Continued)

(52) U.S. Cl.
CPC ...... *A61B 17/320068* (2013.01); *A61B 18/14* (2013.01); *A61B 2017/00929* (2013.01);
(Continued)

(58) Field of Classification Search
CPC ...... A61B 17/320068; A61B 2090/035; A61B 2217/007; A61B 2017/00929; A61B 2017/32007; A61B 2017/320084; A61B 18/14; A61B 2018/00083; A61B 2018/00101; A61B 2018/00446;
(Continued)

(56) References Cited

U.S. PATENT DOCUMENTS

| 3,584,667 | A | * | 6/1971 | Reiland | F16B 23/003 81/460 |
| 4,063,557 | A | | 12/1977 | Wuchinich et al. | |

(Continued)

FOREIGN PATENT DOCUMENTS

| CN | 101214644 A | 7/2008 |
| CN | 102811676 A | 12/2012 |

(Continued)

OTHER PUBLICATIONS

International Search Report and Written Opinion for PCT/IB2017/052382 dated Aug. 17, 2017.

(Continued)

*Primary Examiner* — Walter Yehl
(74) *Attorney, Agent, or Firm* — Middleton Reutlinger

(57) ABSTRACT

An ultrasonic surgical handpiece comprising a thermal diffuser that includes a thermal conductive layer and an electrical insulating layer. The thermal diffuser reduces hot spots that are objectionable to the user. The handpiece may also comprise an anti-rotation feature which distributes force of the metal horn applied to the polymer housing by increasing applied area under torque.

12 Claims, 19 Drawing Sheets

DETAIL A

(51) Int. Cl.
- *A61B 90/00* (2016.01)
- *A61B 17/00* (2006.01)
- *A61B 18/14* (2006.01)
- *A61B 18/00* (2006.01)

(52) U.S. Cl.
CPC .............. *A61B 2017/32007* (2017.08); *A61B 2017/320084* (2013.01); *A61B 2018/00083* (2013.01); *A61B 2018/00101* (2013.01); *A61B 2018/00589* (2013.01); *A61B 2090/035* (2016.02); *A61B 2217/007* (2013.01); *B06B 1/0618* (2013.01)

(58) Field of Classification Search
CPC ........... A61B 2018/00529; A61B 2018/00589; B06B 1/0618; H05K 7/20436; H05K 7/20472
See application file for complete search history.

(56) References Cited

U.S. PATENT DOCUMENTS

| | | | |
|---|---|---|---|
| 4,223,676 A | 9/1980 | Wuchinich et al. | |
| 4,425,115 A | 1/1984 | Wuchinich | |
| 4,516,398 A | 5/1985 | Wuchinich | |
| 4,634,419 A | 1/1987 | Kreizman et al. | |
| 4,734,964 A | 4/1988 | Lane et al. | |
| 4,747,820 A | 5/1988 | Hornlein et al. | |
| 4,750,902 A | 6/1988 | Wuchinich et al. | |
| 4,768,496 A | 9/1988 | Kreizman et al. | |
| 4,827,911 A | 5/1989 | Broadwin et al. | |
| 4,846,790 A | 7/1989 | Hornlein et al. | |
| 4,881,761 A | 11/1989 | Hornlein et al. | |
| 4,921,476 A | 5/1990 | Wuchinich | |
| 4,931,047 A | 6/1990 | Broadwin et al. | |
| 4,978,333 A | 12/1990 | Broadwin et al. | |
| 4,988,334 A | 1/1991 | Hornlein et al. | |
| 5,015,227 A | 5/1991 | Broadwin et al. | |
| 5,190,517 A | 3/1993 | Zieve et al. | |
| 5,221,282 A * | 6/1993 | Wuchinich ..... | A61B 17/320068 606/99 |
| 5,421,829 A | 6/1995 | Olichney et al. | |
| 5,466,020 A | 11/1995 | Page et al. | |
| 5,484,398 A | 1/1996 | Stoddard | |
| D367,323 S | 2/1996 | Carr | |
| 5,492,528 A | 2/1996 | Anis | |
| 5,984,904 A | 11/1999 | Steen et al. | |
| 6,083,191 A | 7/2000 | Rose | |
| 6,177,755 B1 | 1/2001 | Hur | |
| D438,952 S | 3/2001 | Cimino et al. | |
| 6,214,017 B1 | 4/2001 | Stoddard et al. | |
| 6,256,859 B1 | 7/2001 | Stoddard et al. | |
| 6,319,223 B1 | 11/2001 | Wortrich | |
| 6,468,059 B2 | 10/2002 | Haser | |
| 6,499,358 B1 | 12/2002 | Hogan et al. | |
| D477,867 S | 7/2003 | O'Mahony | |
| 6,595,957 B1 | 7/2003 | Griffiths | |
| 6,602,227 B1 | 8/2003 | Cimino et al. | |
| D479,320 S | 9/2003 | O'Mahony | |
| 6,654,999 B2 | 12/2003 | Stoddard et al. | |
| 6,723,110 B2 | 4/2004 | Timm et al. | |
| 7,204,825 B2 | 4/2007 | Cimino et al. | |
| D557,803 S | 12/2007 | Muri | |
| D557,804 S | 12/2007 | Muri | |
| 7,442,168 B2 | 10/2008 | Novak et al. | |
| 7,871,392 B2 | 1/2011 | Sartor | |
| 8,092,475 B2 | 1/2012 | Cotter et al. | |
| 8,118,823 B2 | 2/2012 | Cotter et al. | |
| 8,142,460 B2 | 3/2012 | Cotter et al. | |
| 8,211,103 B2 | 7/2012 | Greep | |
| D675,728 S | 2/2013 | Tout | |
| 8,518,066 B2 | 8/2013 | Cotter et al. | |
| D699,836 S | 2/2014 | Burger | |
| 9,149,291 B2 * | 10/2015 | Parham .......... | A61B 17/320068 |
| 9,421,027 B2 | 8/2016 | Cotter et al. | |
| 2002/0002369 A1 | 1/2002 | Hood | |
| 2004/0075986 A1* | 4/2004 | Schwarz ............ | H05K 7/20454 361/704 |
| 2006/0052774 A1* | 3/2006 | Garrison ............... | A61B 18/042 606/42 |
| 2006/0063973 A1 | 3/2006 | Makower et al. | |
| 2008/0200884 A1 | 8/2008 | Perkins et al. | |
| 2009/0083963 A1* | 4/2009 | Otremba .......... | H01L 23/49562 29/592.1 |
| 2010/0125198 A1* | 5/2010 | Thapliyal ............. | A61B 8/4494 600/439 |
| 2011/0160620 A1* | 6/2011 | Gill ................ | A61B 17/320068 601/2 |
| 2014/0009891 A1* | 1/2014 | Chen ................. | H05K 7/20436 361/720 |
| 2015/0080925 A1 | 3/2015 | Schulte et al. | |
| 2015/0328048 A1 | 11/2015 | Koplin | |
| 2017/0304655 A1 | 10/2017 | Cotter et al. | |
| 2017/0333606 A1 | 11/2017 | Manandhar et al. | |
| 2017/0354429 A1 | 12/2017 | Ketelhohn et al. | |

FOREIGN PATENT DOCUMENTS

| | | |
|---|---|---|
| EP | 1607075 | 12/2005 |
| JP | 63007719 A | 1/1988 |
| JP | H0194841 A | 4/1989 |
| JP | H0199547 A | 4/1989 |
| JP | H05270743 A | 10/1993 |
| JP | H07022248 | 1/1995 |
| JP | 2002253568 A | 9/2002 |
| JP | 2013134983 A | 7/2013 |
| WO | 9308750 A2 | 5/1993 |
| WO | 9513113 A1 | 5/1995 |
| WO | 9517855 | 7/1995 |
| WO | 2004045705 | 6/2004 |
| WO | 2008154803 A1 | 12/2008 |
| WO | 2010057211 A1 | 5/2010 |
| WO | 2011005467 A2 | 1/2011 |
| WO | 2014134292 | 9/2014 |
| WO | 2015061258 | 4/2015 |
| WO | 2016009788 A1 | 1/2016 |
| WO | 2017187345 | 11/2017 |
| WO | 2017203408 | 11/2017 |

OTHER PUBLICATIONS

International Search Report and Written Opinion for PCT/IB2017/052980 dated Jul. 19, 2017.
International Search Report and Written Opinion for PCT/IB2017/053510 dated Nov. 13, 2017.
Partial Search Report for PCT/IB2017/053510 dated Sep. 22, 2017.
Franasiak, Jason M.; Ergonomic Strain in Minimally Invasive Surgery: Addressing the Strain Epidemic; www.jcomjournal.com; vol. 22, No. 6, pp. 267-273, Jun. 2015.
Krautkramer J. and Krautkramer H., Ultrasonic Testing of Materials, 1983.
Berguer, R.; Ergonomic problems associated with laparoscopic surgery; Surgical Endoscopy, 1999 13:466-468; 1999.
Integra Lifesciences Corporation; CUSA Excel Ultrasonic Surgical Aspiration System, CUSA EXcel System User's Guide, 6 pages, 2007.
Integra Lifesciences Corporation; CUSA Excel+ Ultrasonic Surgical Aspirator, 8 pages, 2012.
SonaStar; Ultrasonic surgical aspiration system; Accuracy Matters, 2015.
Transmittal Letter of Related Cases dated Jan. 30, 2019.
European Patent Office, International Search Report and Written Opinion for PCT/IB2017/057145 dated Mar. 15, 2018, dated Mar. 23, 2018, Rijswijk, NL.
Partial Search for International Application No. PCT/IB2017/057145 dated Jan. 31, 2018.
Chinese Search Report for App. No. 201780070585.7 dated Jan. 6, 2021.
Chinese First Office Action for App. No. 201780070585.7 dated Jan. 12, 2021.

(56) References Cited

OTHER PUBLICATIONS

European Extended Search Report for App. No. 20207021.5 dated Mar. 4, 2021.
Japan Patent Office, Notice of Reasons for Rejection for app. No. 2019-512613 dated Aug. 27, 2021.

* cited by examiner

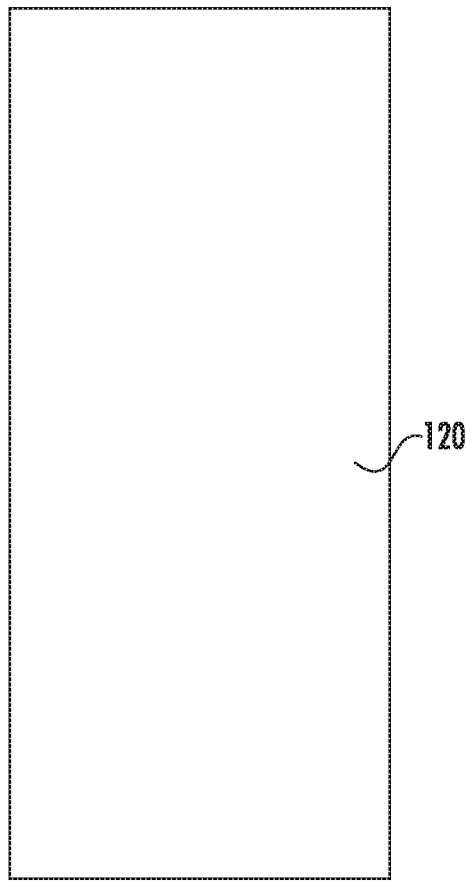
FIG. 9A
FIG. 9B
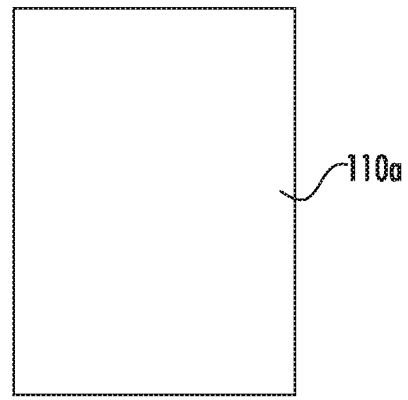
FIG. 10A
FIG. 10B
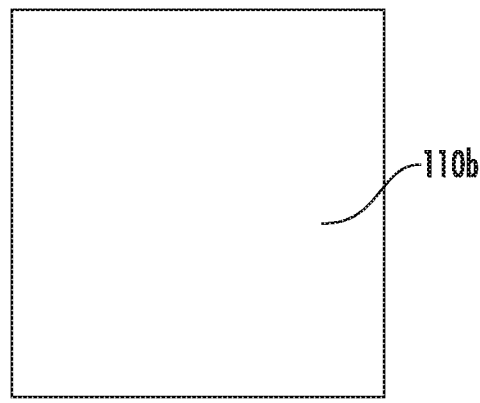
FIG. 11A
FIG. 11B

ULTRASONIC SURGICAL HANDPIECE HAVING A THERMAL DIFFUSER

CROSS-REFERENCE TO RELATED APPLICATIONS

This application claims priority to and benefit under 35 U.S.C. § 119 to U.S. Provisional Application No. 62/422,635, filed Nov. 16, 2016, the entire contents of which are hereby incorporated by reference.

BACKGROUND OF THE INVENTION

Embodiments of the present invention relate generally to surgical handpieces, for example, handpieces in ultrasonic surgical aspirator systems for tissue ablation.

Ultrasonic aspiration has become the standard of care for removal of tumors and diseased tissue in neurosurgery and general surgery. Ultrasonic aspirators are used for ultrasonic fragmentation of tissue at an operation site and aspiration of the tissue particles and fluid away from the site. Typically, ultrasonic surgical aspirators include an ultrasonic transducer supported within a handpiece, an ultrasonically vibrating horn or tip operably connected to the ultrasonic transducer, and a sleeve or flue positioned about the horn. The horn includes a longitudinally extending central bore having one end located adjacent a distal tip and a second end located adjacent the proximal end of the horn. The proximal end of the horn is adapted to engage a vacuum source to facilitate aspiration of fluid. The flue is positioned about the horn to define an annular passage. Irrigation fluid is supplied through the annular passage around the horn to the surgical site where it mixes with blood and tissue particles and is aspirated through the bore in the horn. By mixing the irrigation fluid with the blood and tissue particles, coagulation of the blood is slowed down and aspiration thereof is aided. When the longitudinally vibrating tip in such an aspirator is brought into contact with tissue, it gently, selectively, and precisely fragments and removes the tissue. U.S. Pat. Nos. 5,015,227 and 4,988,334 disclose such ultrasonic surgical devices and are incorporated herein by reference. A known ultrasonic aspirator on the market is the CUSA® Excel Ultrasonic Surgical Aspirator (Integra LifeSciences Corporation, Plainsboro, N.J., U.S.A.).

The handpiece typically has a housing encasing a transducer on which a surgical tip is fastened. The housing is commonly made of a polymeric material for electrical safety, especially with high-voltage electrosurgery levels (e.g., 1750 Vp) applied to the metallic body of the transducer and surgical tip. CUSA Excel 36 kHz handpiece is described in U.S. Pat. No. 6,214,017 to Stoddard, et al., and 23 kHz handpiece is described in U.S. Pat. Nos. 4,425,115 and 4,223,676 to Wuchinich et al.

Polymer housings of the handpieces in existing systems yielded concentrated thermal rise associated with the transducer, or so called "hot spots" that are felt by the surgeon whose hand tactile sensitivity is acute during surgery. Ultrasonic transducers with metallic housings do not have these complications due to strength and diffusion of hot spots with thermally conductive cases, but the electrical safety requirements given simultaneous ultrasonic and electrosurgery power application necessitate polymer housings.

In addition, polymer housings sometimes failed due to rotation of the transducer, as a result of low-allowed stress of plastic and concentrated stress of mating metallic anti-rotation constraints. The commercial CUSA Excel 36 kHz handpiece is magnetostrictive and has a hex feature that can fail under misuse, such as the nurse tightening or loosening the surgical tip while only holding the internal horn with the housing. Many of the failed handpieces are twisted in the housing. The transducer vibrates along its length and stepped horns and specialty profiles of reduced diameter amplify vibration. Often, the surgical tip is a single use device which must be attached under high torque (e.g. 25-65 in-lb) to the internal ultrasonic horn of the transducer to ensure adequate acoustic coupling. The internal ultrasonic horn of the transducer commonly has flats or hex features, such as a nut, for holding the transducer while tightening the surgical tip with a special torque wrench. In addition, a torque base is provided as a platform to hold the handpiece for fastening and loosening a surgical tip. It is found in practice that sometimes the nurse or clinician does not employ the torque base to hold the transducer while tightening the surgical tip before use or loosening it following the procedure. Piezoelectric transducers have PZT (lead-zirconate-titanate) ceramics that are electrically connected by wires to external cables, which can break when twisted. Magnetostrictive transducers depend on positioning of the transducer stack in the magnetic field to ensure adequate power. Effective anti-rotation constraints are needed, but these must not rigidly couple ultrasound during vibration to the housing, because of loss of power, errant heating, and potential for audible noise from sub-harmonics. Hex features alone on internal horns with mating hexagonal recesses on housings could fail structurally at the applied torque needed for surgical tips.

Hence, those skilled in the art have recognized a need for surgical handpieces with improved thermal performance and structural stability. Embodiments of the present invention fulfill this need and others.

SUMMARY OF THE INVENTION

Briefly and in general terms, embodiments of the present invention disclose high-powered compact ultrasonic transducers with electro surgery coagulation that incorporate a conductive thermal diffuser to eliminate objectionable hot spots from the surgeon's hands in prolonged usage, such as in brain tumor removal and liver resection.

In some embodiments of the invention, for example, a surgical handpiece may comprise a housing, an electrical component within the housing, and/or a thermal diffuser disposed between the housing and the electrical component and comprising a thermal conductive layer and an electrical insulating layer. In various embodiments, the thermal conductive layer may be closer to the housing than the electrical insulating layer.

In addition, in various embodiments, the thermal conductive layer may comprise a plurality of thermal conductive material pieces. In some embodiments, there may be an overlap between two thermal conductive material pieces. In various embodiments, the housing may have an elongated body and the thermal diffuser may be in a cylindrical or partially cylindrical form that fits in the elongated body around the electrical component. Moreover, in some embodiments, the thermal conductive layer may be made of a material selected from the group consisting of copper, aluminum, nickel, silver, gold and alloys thereof. In various embodiments, the electrical insulating layer may be made of a material selected from the group consisting of polytetrafluoroethylene, polycarbonate, polypropylene and combinations thereof. In some embodiments, the thermal conductive layer and the electrical insulating layer may be bonded with an adhesive. In various embodiments, the housing may be made of an electrical insulating material. In addition, in some embodiments, the electrical component may be an ultrasonically powered transducer.

In some embodiments, a surgical handpiece may comprise a housing having an elongated body along a longitudinal axis. In various embodiments, an ultrasonically powered transducer may be positioned within the elongated body of the housing. In addition, in some embodiments, a thermal diffuser may be disposed between the elongated body of the housing and the transducer. In various embodiments, the thermal diffuser may comprise a thermal conductive layer and an electrical insulating layer. In some embodiments, the thermal conductive layer may be closer to the elongated body of the housing than the electrical insulating layer. In various embodiments, the thermal diffuser may be disposed adjacent the elongated body of the housing and may be radially spaced outwardly from the transducer.

In addition, in various embodiments, the thermal conductive layer may comprise a plurality of thermal conductive material pieces. In some embodiments, there may be an overlap between two thermal conductive material pieces. In various embodiments, the thermal conductive layer may be made of at least copper and the electrical insulating layer may be made of at least polytetrafluoroethylene. Moreover, in some embodiments, the thermal conductive layer and the electrical insulating layer may be bonded with an adhesive.

In various embodiments, an ultrasonic surgical handpiece may comprise an elongated housing having an inner surface, a longitudinal axis, and/or a housing engagement portion on the inner surface. In some embodiments, the housing engagement portion may have a transverse section that includes a central recess, a plurality of pointed recesses pointing radially outward from the central recess and spaced evenly about the longitudinal axis, and/or convex arcs joining adjacent pointed recesses. In various embodiments, an ultrasonic horn may be contained coaxially within the housing and include an outer surface and a horn engagement portion on the outer surface. Moreover, in some embodiments, the horn engagement portion may have a transverse section that includes a central portion, a plurality of pointed protrusions extending radially outward and spaced evenly about the longitudinal axis, and/or concave arcs joining adjacent pointed protrusions. In various embodiments, each of the pointed protrusions may correspond in shape and may be engageable with each of the pointed recesses.

In some embodiments, each convex arc may have a side wall which is generally parallel with the longitudinal axis, and each concave arc may have a side wall which is generally parallel with the longitudinal axis. In various embodiments, the housing engagement portion may comprise at least three pointed recesses, and the horn engagement portion may comprise at least three pointed protrusions. In some embodiments, the housing engagement portion may comprise five to seven pointed recesses, and the horn engagement portion may comprise five to seven pointed protrusions. In addition, in some embodiments, at least one pointed recess may have a recess tip portion that is rounded or curved or constitutes a portion of a sphere. In various embodiments, at least one pointed protrusion may have a protrusion tip portion that is rounded or curved or constitutes a portion of a sphere.

In accordance with aspects of some embodiments of the present invention, there is provided a surgical handpiece which comprises a housing, an electrical component within the housing, and a thermal diffuser disposed between the housing and the electrical component. The thermal diffuser comprises a thermal conductive layer and an electrical insulating layer, wherein the thermal conductive layer is closer to the housing than the electrical insulating layer. In more detailed aspects, the thermal conductive layer comprises a plurality of thermal conductive material pieces, and there is an overlap between two thermal conductive material pieces.

In further detailed aspects, the housing of the surgical handpiece has an elongated body and the thermal diffuser is in a cylindrical or partially cylindrical form that fits in the elongated body around the electrical component.

In accordance with other aspects of embodiments of the present invention, an anti-rotation feature is provided for distributing force of the metal horn applied to the polymer housing by increasing applied area under torque, thereby reducing failure of surgical devices due to rotation of the transducer during tightening or loosening of surgical tips.

In more detailed aspects, there is provided an ultrasonic surgical handpiece which comprises an elongated housing having an inner surface, a longitudinal axis, and a housing engagement portion on the inner surface, the housing engagement portion having a transverse section that includes a central recess, a plurality of pointed recesses pointing radially outward from the central recess and spaced evenly about the longitudinal axis, and convex arcs joining adjacent pointed recesses; an ultrasonic horn contained coaxially within the housing and having an outer surface and a horn engagement portion on the outer surface, the horn engagement portion having a transverse section that includes a central portion, a plurality of pointed protrusions extending radially outward and spaced evenly about the longitudinal axis, and concave arcs joining adjacent pointed protrusions; and wherein each of the pointed protrusions corresponds in shape and is engageable with each of the pointed recesses.

In a further detailed aspect, each convex arc of the housing engagement portion has a side wall which is generally parallel with the longitudinal axis, and each concave arc of the horn engagement portion has a side wall which is generally parallel with the longitudinal axis. In addition, at least one pointed recess may have a recess tip portion constituting a portion of a sphere, and at least one pointed protrusion may have a protrusion tip portion constituting a portion of a sphere.

Other features and advantages of the embodiments of the present invention will become more apparent from the following detailed description of the invention, when taken in conjunction with the accompanying exemplary drawings.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

Embodiments of the present invention are described herein with reference to the drawings, in which:

FIG. 9A is a top plan view of a polytetrafluoroethylene (PTFE) layer of a thermal diffuser composite sheet in accordance with embodiments of the present invention;

FIG. 9B is a side view of the PTFE layer of FIG. 9A;

FIG. 10A is a top plan view of a copper tape component of the thermal diffuser composite sheet;

FIG. 10B is a side view of the copper tape component of FIG. 10A;

FIG. 11A is a top plan view of another copper tape component of the thermal diffuser composite sheet;

FIG. 11B is a side view of the copper tape component of FIG. 11A;

DETAILED DESCRIPTION OF THE PREFERRED EMBODIMENTS

Figure 1:
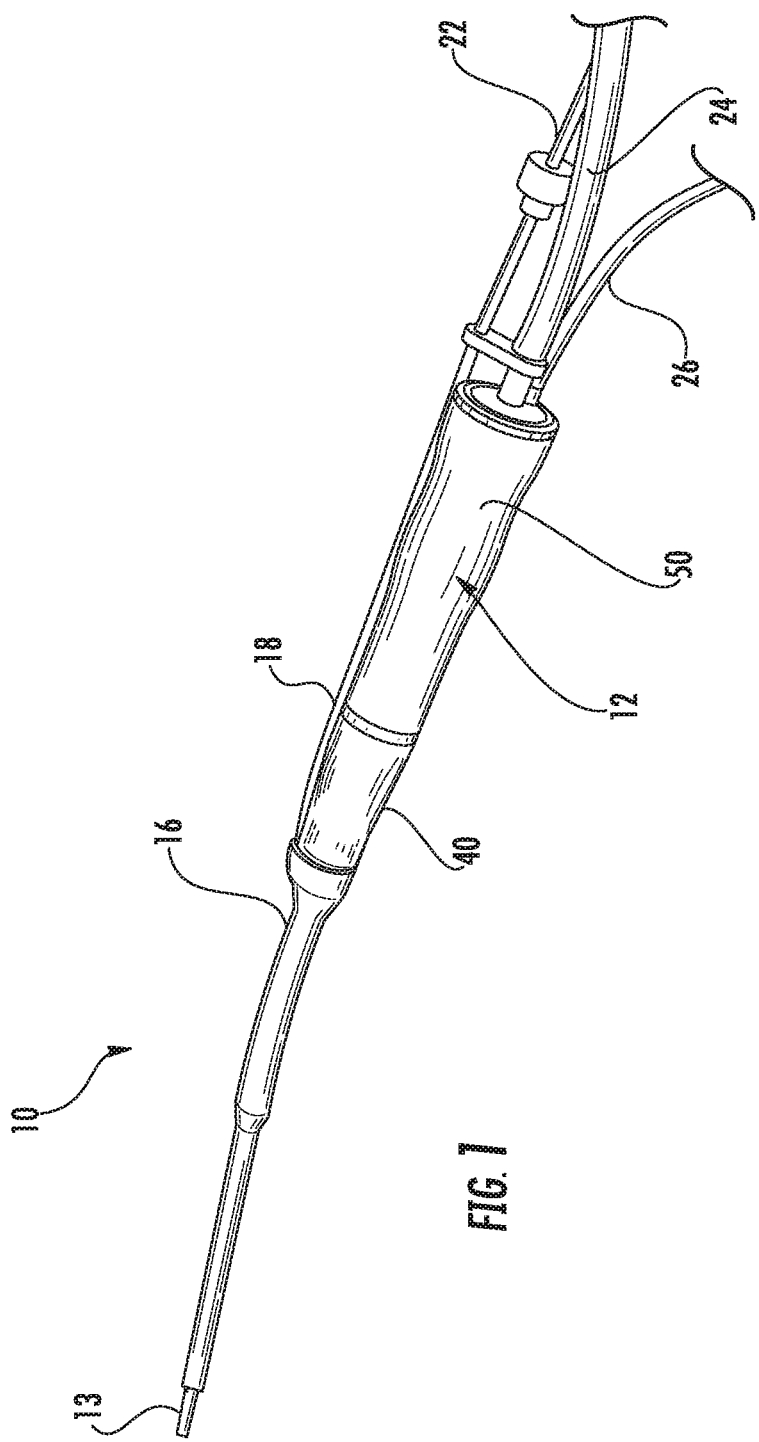
FIG. 1 is a perspective view of an ultrasonic surgical apparatus in accordance with embodiments of the present invention.

Embodiments of the presently disclosed surgical handpieces will now be described in detail with reference to the drawings, in which like reference numerals designate identical or corresponding elements in each of the several views. As used herein, the term "distal" refers to that portion of the instrument, or component thereof which is farther from the user while the term "proximal" refers to that portion of the instrument or component thereof which is closer to the user during normal use. The terms "ultrasonic horn," "ultrasonic tip," "ultrasonic aspirating tip," "ultrasonic surgical aspirating tip," "aspirating tip," "ultrasonic surgical tip," "surgical tip", "horn" and "tip" are used herein interchangeably. The terms "housing," "handpiece housing," and "transducer housing" are used herein interchangeably. The terms "internal ultrasonic horn" and "internal horn" are used herein interchangeably.

Figure 2:
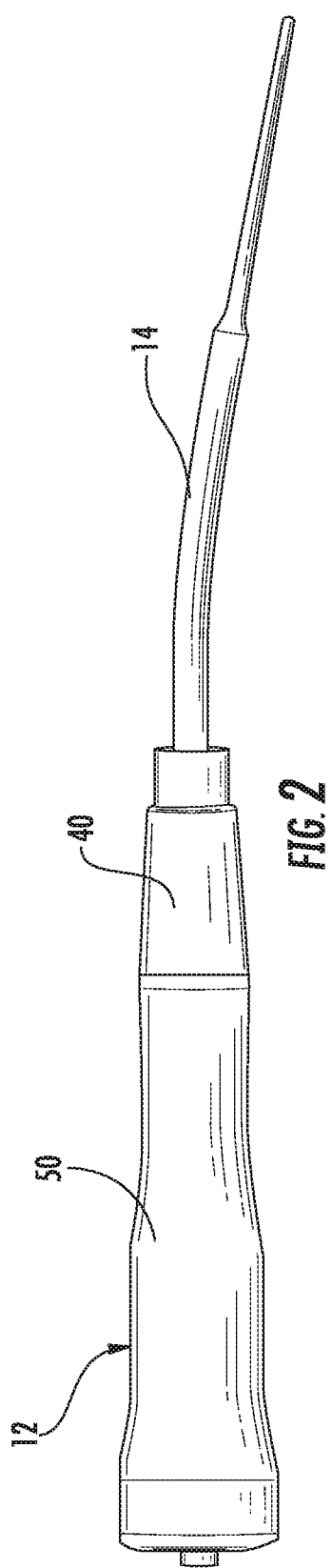
FIG. 2 is a side view of an ultrasonic surgical handpiece in accordance with embodiments of the present invention with a nosecone and surgical tip attached to it.
Figure 3:
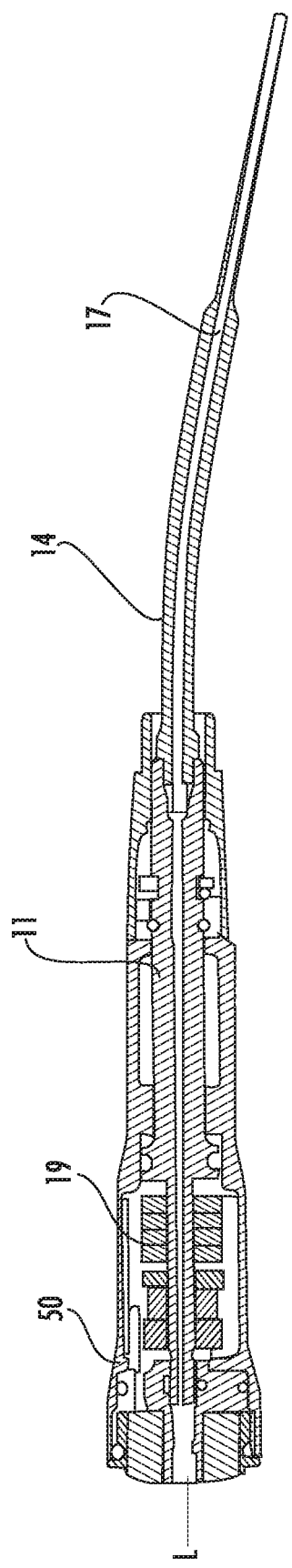
FIG. 3 is a longitudinal-sectional view of the ultrasonic surgical handpiece of FIG. 2.

FIGS. 1-3 show an ultrasonic surgical apparatus 10 for ultrasonically fragmenting and aspirating tissue. Generally the ultrasonic surgical apparatus 10 includes a handpiece 12 for use by a surgeon to direct fragmentation. The handpiece 12 encases a transducer 19 coupled to an internal ultrasonic horn 11 to which a surgical tip 14 is fastened. The transducer converts electrical energy into mechanical motion. The surgical tip 14 can be powered by the transducer 19 and be ultrasonically actuated to fragment tissue and suction effluent via a central channel 17. The internal ultrasonic horn 11 includes a connecting point for the surgical tip 14 and transfers the vibrations from the transducer 19 to the surgical tip 14 to fragment tissue during surgery. A distal end portion 13 of a surgical tip 14 extends beyond a distal end of a flue 16. The internal ultrasonic horn 11 and the surgical tip 14 may be made of titanium or other conventional materials known in the art.

A cooling and irrigation system which provides cooling fluid to the ultrasonic horn 14 is provided for maintaining temperature within an acceptable range. The handpiece 12 includes a housing 50, which may be formed of a sterilizable plastic, metal or other suitable materials or a combination thereof. The flue 16 provides a path for irrigation fluid or liquid and connects to the distal end of the handpiece 12. The flue 16 typically connects to the handpiece 12 via a nosecone 40. The flue 16 may include or attach to a flue tube 18. The nosecone 40 connects to the housing 50 and covers the proximal end portion of the surgical tip 14.

An irrigation tube 22 connects to the flue tube 18 upstream and supplies irrigation fluid through the flue tube 18 to an operative site during surgery. An aspiration tube 24 provides suction and a path for aspiration from the operative site to a collection canister (not shown). An electrical cable 26 provides power to the apparatus or provides switching connections.

Figure 4:
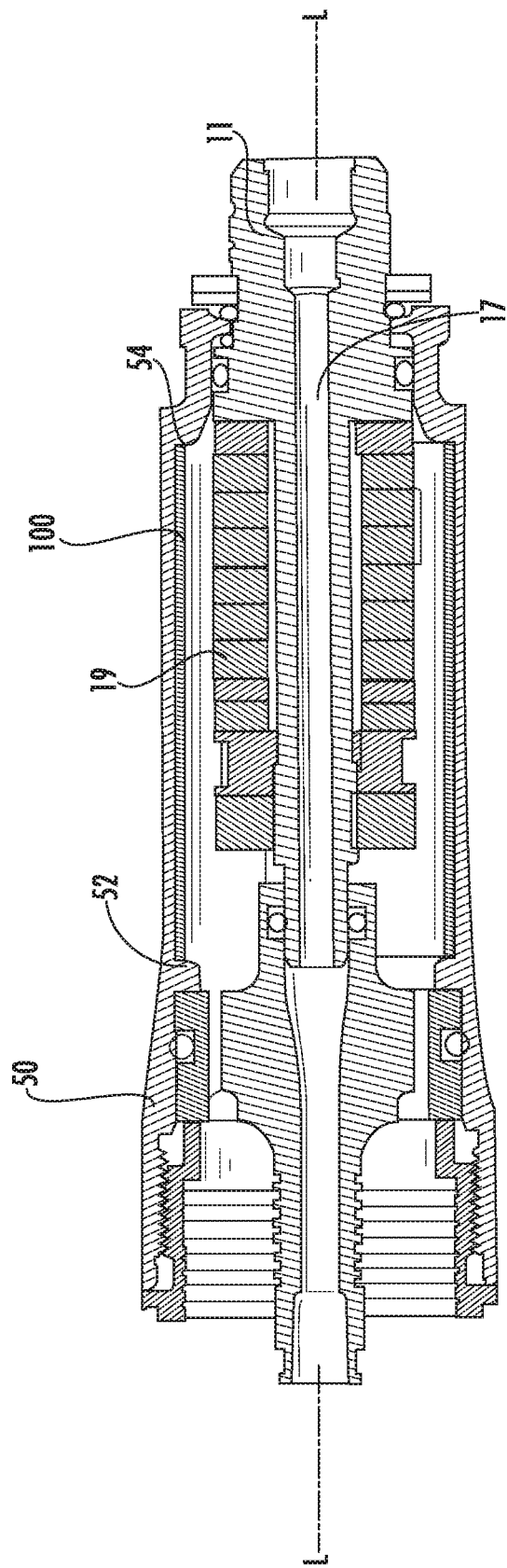
FIG. 4 is another longitudinal-sectional view of a portion of the ultrasonic surgical handpiece of FIG. 2.
Figure 5:
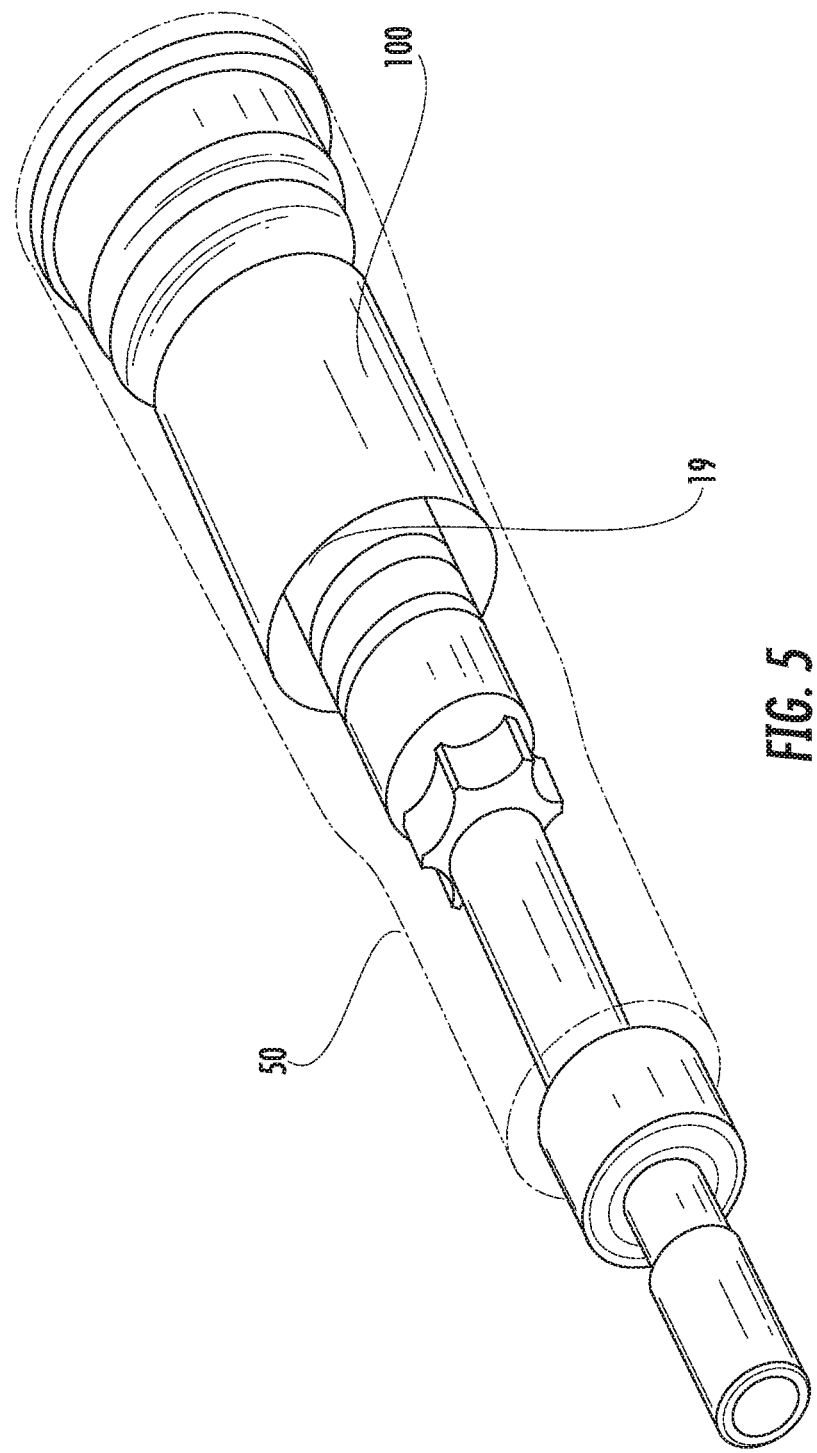
FIG. 5 is a perspective view of a portion of the ultrasonic surgical handpiece of FIG. 2 with the handpiece housing shown in phantom.
Figure 6:
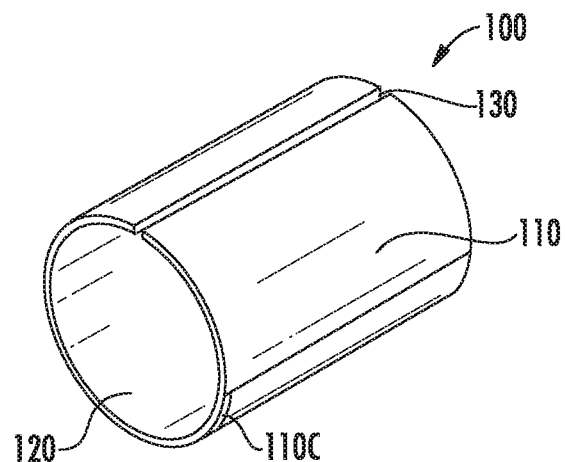
FIG. 6 is a perspective view of a thermal diffuser in accordance with embodiments of the present invention.
Figure 7:
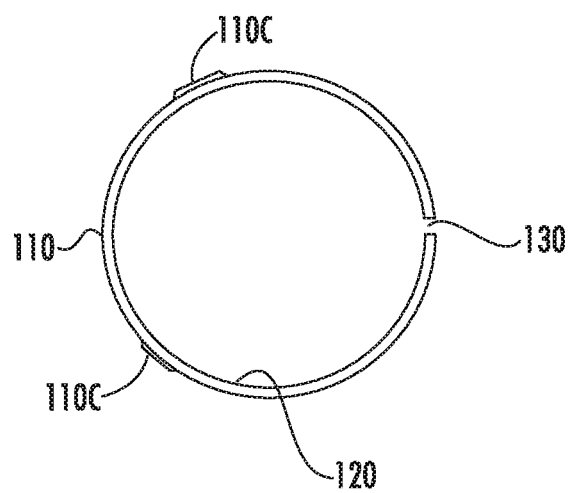
FIG. 7 is a cross-sectional view of the thermal diffuser of FIG. 6.
Figure 8:
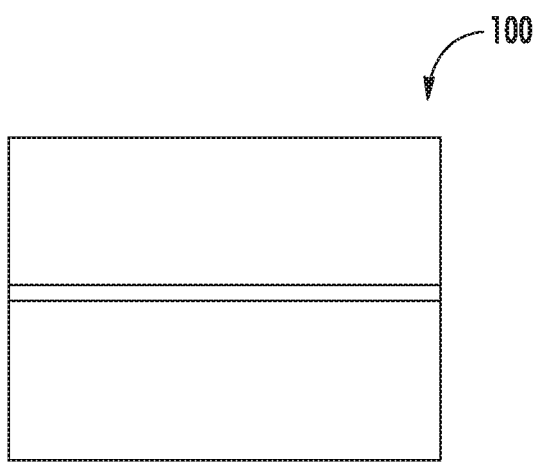
FIG. 8 is a side view of the thermal diffuser of FIG. 7.
Figure 12:
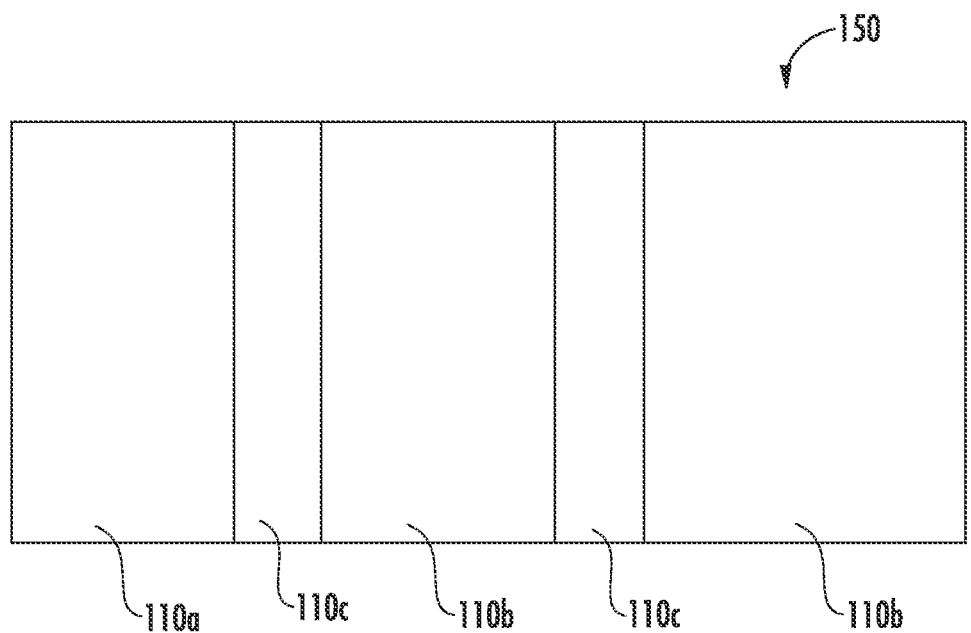
FIG. 12 illustrates a thermal diffuser composite sheet.
Figure 13:
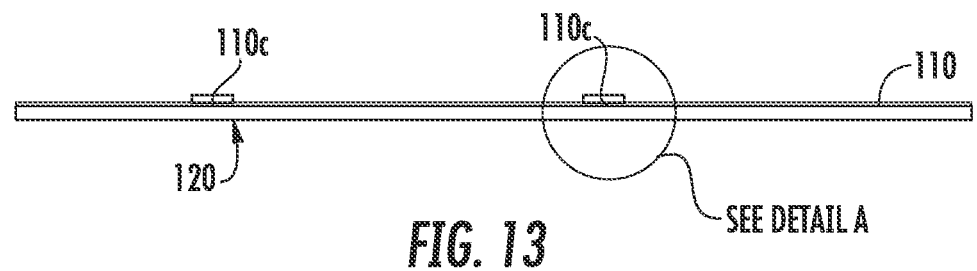
FIG. 13 is a side view of the thermal diffuser composite sheet of FIG. 12.
Figure 14:
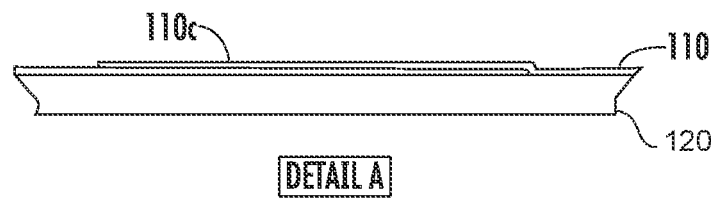
FIG. 14 is a detailed view of a section of the thermal diffuser shown in FIG. 13.

As shown in FIGS. 4 and 5, the handpiece 12 has an elongated housing 50 and an electrical component, such as the ultrasonically powered piezoelectric transducer 19, within the housing 50. The handpiece 12 also has a thermal diffuser 100 within the housing 50. The thermal diffuser 100 is disposed between the housing 50 and the electrical component 19. The thermal diffuser 100 is in a cylindrical form or a substantially or partially cylindrical form that fits in the elongated body of the housing 50 around the internal electrical component 19.

The housing has a proximal shoulder 52 and a distal shoulder 54 on the inner surface of the housing. The proximal shoulder 52 faces generally distally and the distal shoulder 54 faces generally proximally. The shoulders 52, 54 are formed radially about the longitudinal axis L of the housing 50 and form a sitting space in between for the thermal diffuser 100 to snugly sit in and stay in place around the inner surface of the housing 50. The housing is made of a material that is electrical insulating and preferably also heat resistant. For example, the housing may be made of polyphenylsulfone.

FIGS. 6 to 14 show an exemplary embodiment of a thermal diffuser of the present invention. The thermal diffuser 100 is made from a thermal diffuser composite sheet 150 that comprises a thermal conductive layer 110 and an electrical insulating layer 120. The thermal conductive layer 110 comprises thermal conductive material pieces 110a, 110b with overlapping areas 110c between pieces.

To make the thermal diffuser, take a sheet of an electrical insulating material 120, such as a sheet of polytetrafluoroethylene (PTFE), of suitable dimensions. Take thermal conductive material pieces 110a, 110b, such as copper foil tape, of suitable dimensions. The thermal conductive material pieces may be of the same or different sizes. Clean the PTFE sheet with a cleanser, for example, isopropyl alcohol, to provide an adhesive ready surface. Lay and bond copper tape pieces on the adhesive ready surface of PTFE sheet. Do it piece by piece with an overlapping area 110c of about 5/16 inches between thermal conductive material pieces 110a, 110b. All pieces of copper tape on the PTFE sheet are then smoothed by a plastic rod. The edges of the copper tape or PTFE piece are then cut so that the two layers match in size and shape to provide a thermal diffuser composite sheet 150.

Figure 15:
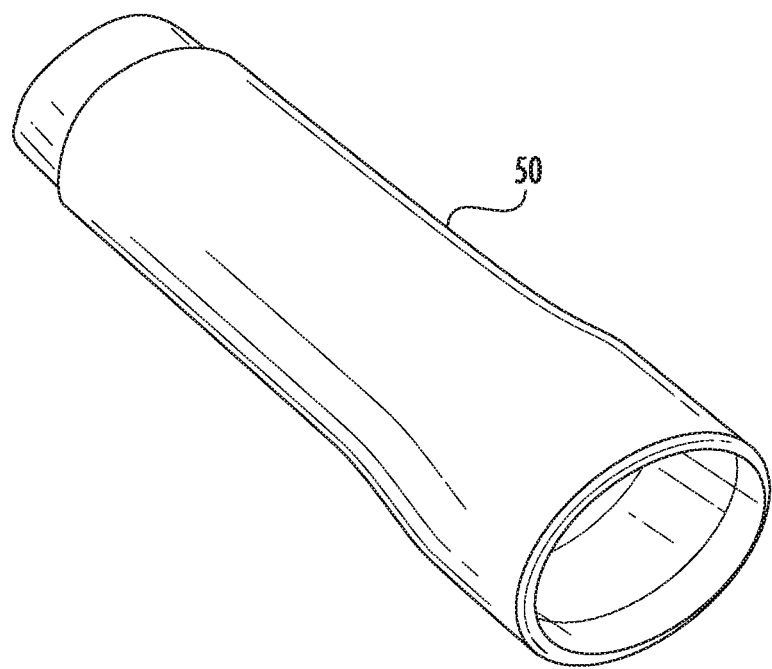
FIG. 15 is a perspective view of a handpiece housing.
Figure 16:
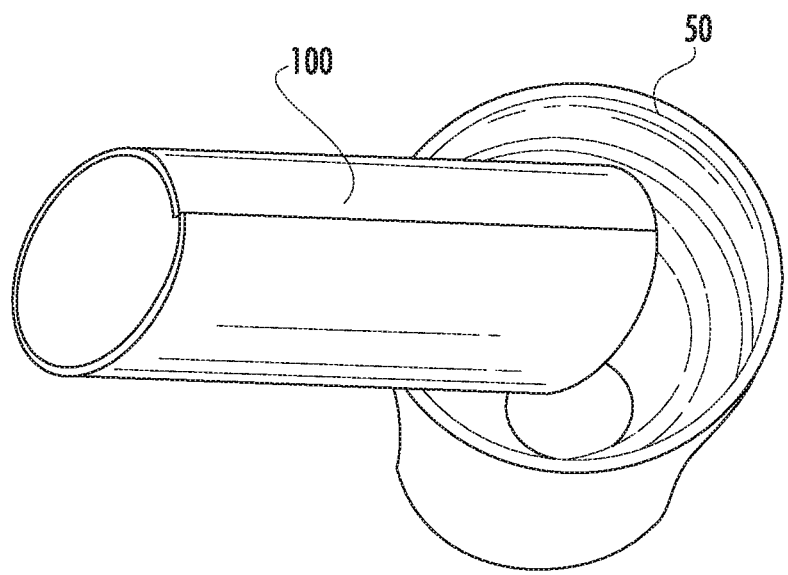
FIGS. 16 to 18 illustrate steps of placing a thermal diffuser in the handpiece housing of FIG. 15.
Figure 17:
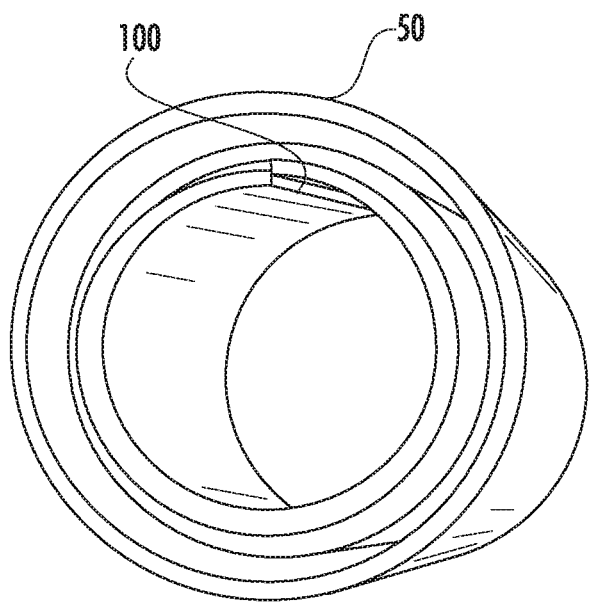
Figure 18:
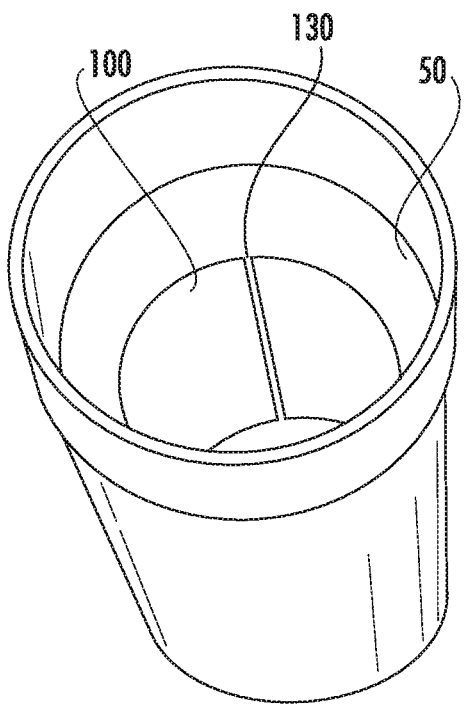

The next steps are to make the thermal diffuser composite sheet 150 into a thermal diffuser and place it into a handpiece housing. An exemplary embodiment of a housing is shown in FIG. 15. Bend or roll the thermal diffuser composite sheet 150 by a plastic rod to form a thermal diffuser 100 in a generally cylindrical form as shown in FIG. 16. The thermal conductive layer is the outer layer of the cylinder and the electrical insulating layer is the inner layer of the cylinder. The strips of overlapping areas 110c extend longitudinally on the thermal diffuser. Then put the thermal diffuser into the housing 50 as shown in FIGS. 17 and 18. Optionally, use a heat gun and a plastic rod to smooth the thermal diffuser inside of the transducer housing. Finally, check the disposition of the thermal diffuser inside of the transducer housing.

The thermal diffuser cylinder tends to spring out in the housing and stays in place in the housing, for example, in the space between the shoulders 52, 54. Once put in the housing, the thermal diffuser cylinder opens, conforms to the inner surface of the housing, and stays in place with the ends touching or nearly touching with a small gap 130, as illustrated in FIG. 18. The thermal conductive layer 110 within the handpiece is closer to the housing 50 than the electrical insulating layer 120. The thermal conductive layer 110 faces the housing 50 and the electrical insulating layer 120 faces the electrical component 19.

Although the embodiment shown in the drawings has a thermal conductive layer that comprises three thermal conductive materials pieces, it is understood that the thermal conductive layer may comprise or consist of a single sheet of thermal conductive material or a plurality of thermal conductive material pieces. There may be any suitable amount of overlap between thermal conductive material pieces or no overlap at all, and there may be gaps between thermal conductive material pieces. Likewise, the electrical insulating layer may comprise or consist of a single sheet of electrical insulating material as illustrated in the drawings or a plurality of electrical insulating material pieces, and there may be any suitable amount of overlap between the electrical insulating material pieces or no overlap at all and there may be gaps between the electrical insulating material pieces. The thermal conductive layer and the electrical insulating layer do not need to be perfectly continuous layers to perform their respective functions. However, it is believed the embodiment as shown, which includes three thermal conductive material pieces with overlapping areas between the pieces, will prevent deformation that may be caused by thermal expansion.

The thermal conductive layer is made of a material that exhibits high thermal conductivity, such as metals, carbons such as graphite, ceramics and certain composites. Materials of high thermal conductivity are widely used in heat sink applications. The thermal conductive material of the thermal conductive layer preferably has a thermal conductivity value that is higher than about 90 W/m·K and more preferably higher than about 200 W/m·K. Examples of thermal conductive materials include copper, aluminum, nickel, silver, gold and alloys thereof such as aluminum alloy.

The electrical insulating layer is made of an electrical insulating material. Electrical insulating materials are typically considered to be materials with a surface resistivity greater than $10^{12}$ Ω/sq (ohms per square). Material like glass, porcelain, paper, polymeric materials such as rubber, rubber-like polymers and plastics, and composite materials are good electrical insulators. Examples of electrical insulting materials include polytetrafluoroethylene (PTFE), polycarbonate, polypropylene, polyetherimide, polyphenylsulfone, and combinations thereof.

The thermal conductive layer and the electrical insulating layer may be bonded with an adhesive or be connected by mechanical means or other means known in the art. If metal tape such as copper tape is used as the thermal conductive layer, no separate adhesive is necessary to bond it with the electrical insulating layer, as the copper tape is backed with an adhesive that may electrically conductive or non-conductive. It is also contemplated that the thermal conductive layer and the electrical insulating layer do not need to be bonded or connected by any adhesive or particular means. The layers may stay in contact after they are rolled up and inserted into the housing.

Suitable adhesives include, but are not limited to, acrylic, epoxy, aramid-based, urethane-based, polyamide-based, polyethylene-based, ethylene-vinyl acetate (EVA)-based, polyester-based, and polyvinyl chloride (PVC)-based adhesives. The layers may also be bonded with an adhesive tape, such as a double-sided adhesive tape.

The exemplary embodiment of the thermal diffuser described above is a PTFE plus copper thermal diffuser. Copper tape with an adhesive side is used as the thermal conductive layer. The copper tape is backed with a PTFE polymer sheet. The copper is placed on the PTFE sheet and kept between the housing and PTFE sheet. The PTFE sheet prevents the copper from contacting and electrically shorting any of the elements of the transducer stack, such as the terminal. Additionally, PTFE has low coefficient of friction if any elements of the vibrating stack contact this material, although such contact is avoided by design. The thermal diffuser can be made from a PTFE sheet having a thickness of about 0.020 inches, and a copper foil tape that has a nonconductive adhesive backing and a total thickness of about 0.0029 inches.

The thermal conductive layer, the electrical insulating layer, and the thermal diffuser composite sheet formed from the two layers may have any appropriate thicknesses as can be readily determined by those skilled in the art, taking into consideration a number of factors including, but not limited to, the desired thermal conductive and electrical insulating properties, the available space in the handpiece housing to accommodate the thermal diffuser, and the necessary flexibility of the thermal diffuser composite sheet to be rolled up to form a generally or substantially cylindrical form or any other desired form. For example, the thermal conductive layer may have a thickness of less than about 0.1 inches and preferably less than 0.05 inches, for example, in the range of from 0.001 to 0.010 inches, and the electrical insulating layer may have a thickness of less than about 0.1 inches and preferably less than about 0.05 inches, for example, in the range of 0.01 to 0.05 inches.

Suitable dimensions of the thermal diffuser composite sheet and the thermal diffuser formed therefrom can also be readily determined by those skilled in the art, depending on a number of factors, such as the size and shape of the medical device that contain the thermal diffuser and the desired thermal diffusing effects. The thermal conductive layer and the electrical insulating layer in a thermal diffuser do not need to match perfectly in size or shape so long as they overlap and provide adequate thermal dissipation and prevent short circuiting.

Although as illustrated, the thermal diffuser would be touching the inner surface of the handpiece housing once the thermal diffuser cylinder springs out, it is believe that the thermal diffuser would work without contact with the housing or the transducer. The thermal diffuser may be bonded to the housing and/or the transducer, but it is not necessary.

It is also contemplated that the thermal conductive layer and the electrical insulating may be placed into the housing separately or sequentially. For example, a thermal conductive cylinder may be inserted into the housing and positioned in place first, and then an electrical insulating cylinder is inserted into the thermal conductive sleeve formed in the housing. The thermal diffuser may have multiple thermal conductive layers and multiple electrical insulating layers arranged in any suitable order.

After the thermal diffuser composite sheet is rolled up and before the thermal diffuser is placed in the housing, the ends of the thermal diffuser may be in contact or not in contact or may overlap to various degrees. Likewise, after the thermal diffuser is placed in the housing, the ends of the thermal diffuser may be in contact or not in contact or may overlap to various degrees. The loose end of the thermal diffuser may be bonded to the cylindrical body with an adhesive or by mechanical or chemical means, but it is not necessary.

Without being bound by any particular theory, it is believed that the copper is not a simple heat sink, as it is not contacting the thermally heated elements, such as the terminals, or conducting. Different thickness layers of copper were tested, but it was learned that a single 76 micrometer or 0.003 inch thick sheet with minimal overlap was sufficient. Doubling the thickness had little effect on temperature at the housing, whereas heat sink size and volume in conventional electrical designs, such as for transistor and power supplies, are surface area and volume dependent and have influence on dissipation of heat. Instead, the copper, which is thermally conductive, diffuses radiant and convective heat from the hot spots of the transducer stack which transits the space between the transducer stack or terminal and the PTFE sheet to the copper. The concentrated radiant and convective heat would attempt to concentrate at the copper, but it is highly thermally conductive so the heat diffuses about the copper. If the heat were in the form of an electric field or conducted current it would diffuse to form an equipotential surface about the whole surface of the copper. An analogy is that the copper diffuses the heat in a way that would be an equipotential temperature. However, some heat is lost to the surroundings, and some heat still conducts to the housing. The copper sheet is a highly thermally conductive diffuser of concentrated convective and radiant heat arriving to its surface, thereby reducing the temperature associate with hot spots.

Figure 19:
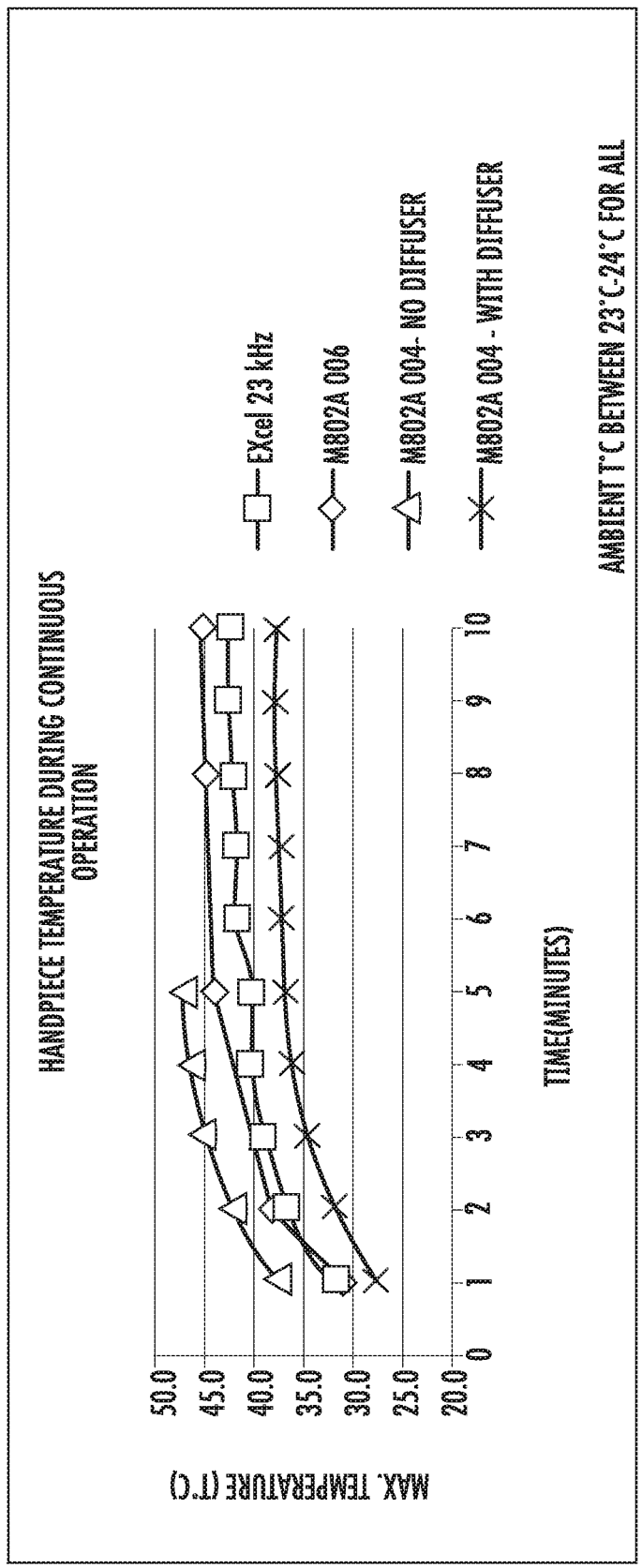
FIG. 19 shows the test results of handpiece temperatures during continuous operation.
Figure 20:
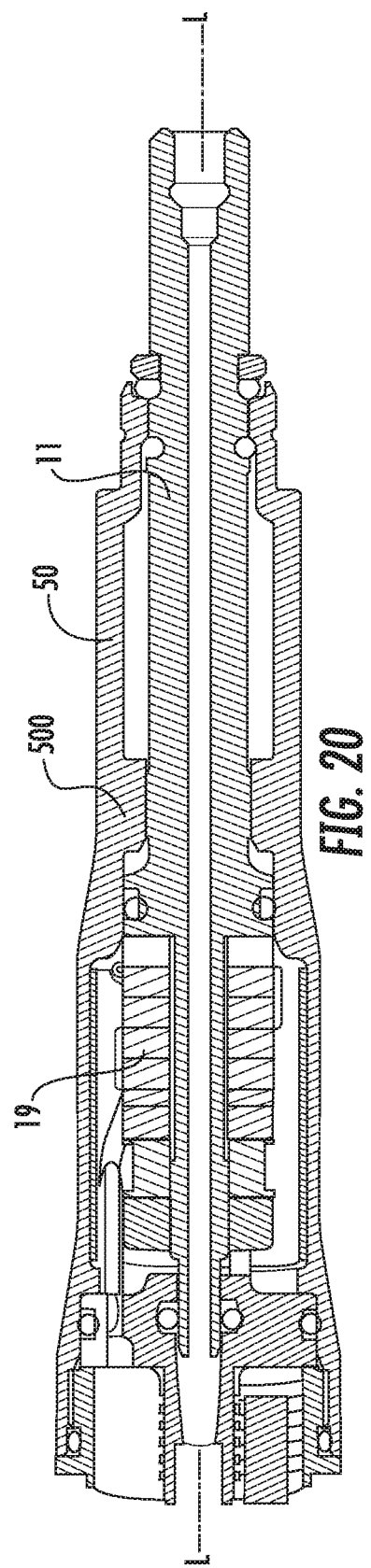
FIG. 20 is a longitudinal-sectional view of an ultrasonic surgical handpiece in accordance with embodiments of the present invention.
Figure 21:
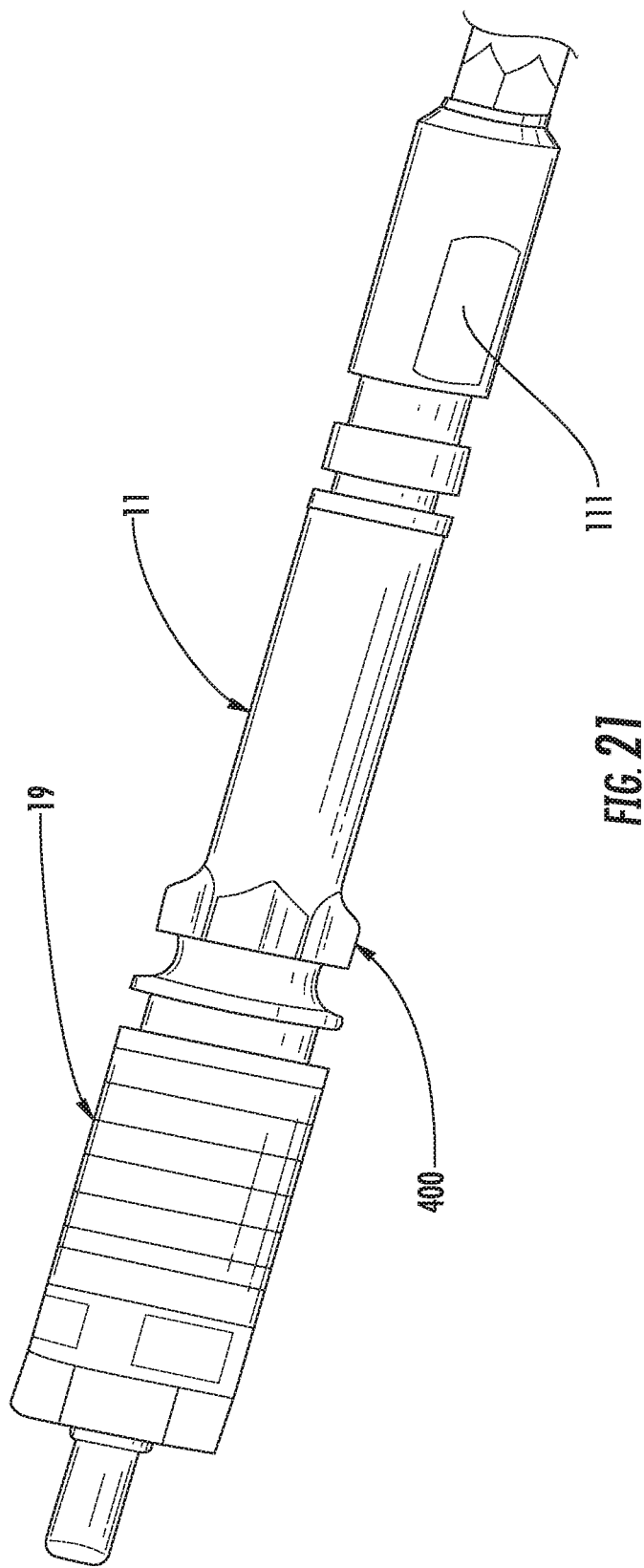
FIG. 21 is a perspective view of an ultrasonic transducer including an internal ultrasonic horn in accordance with embodiments of the present invention.
Figure 22:
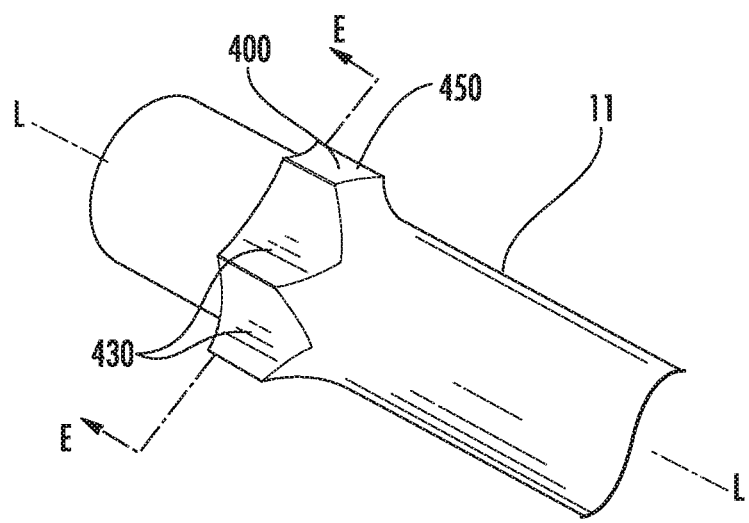
FIG. 22 is a perspective view of a portion of the internal ultrasonic horn shown in FIG. 21.
Figure 23:
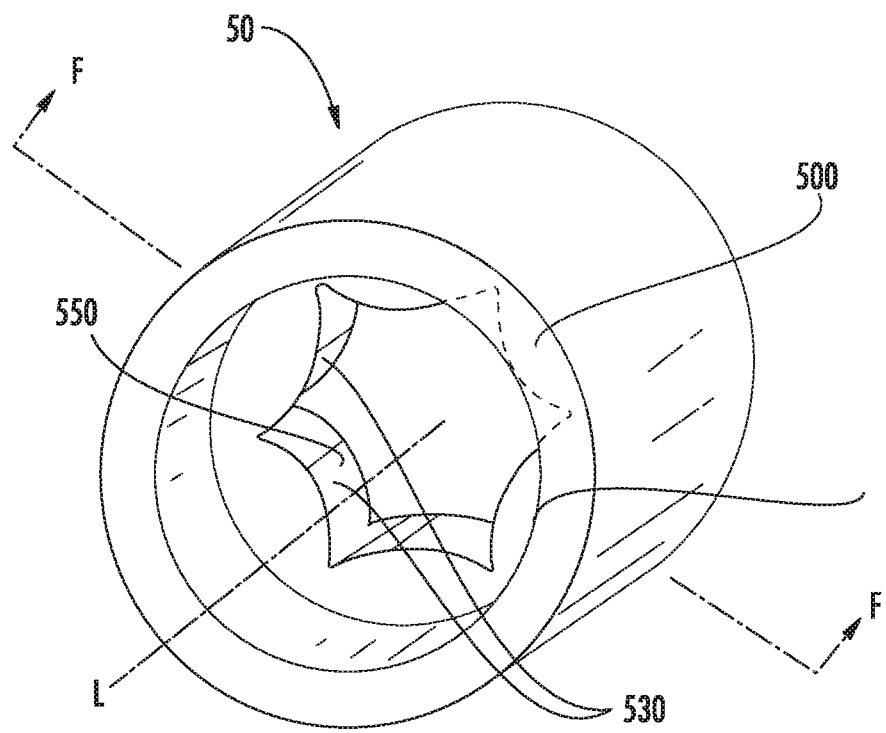
FIG. 23 illustrates a housing engagement portion of a handpiece housing.
Figure 24:
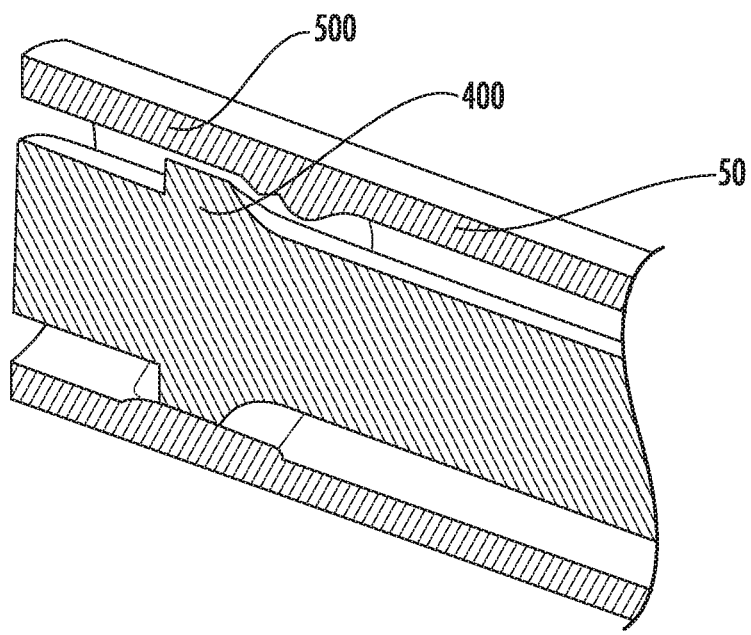
FIG. 24 is a longitudinal-sectional view of a portion of the handpiece housing and internal ultrasonic horn in an assembled state.
Figure 25:
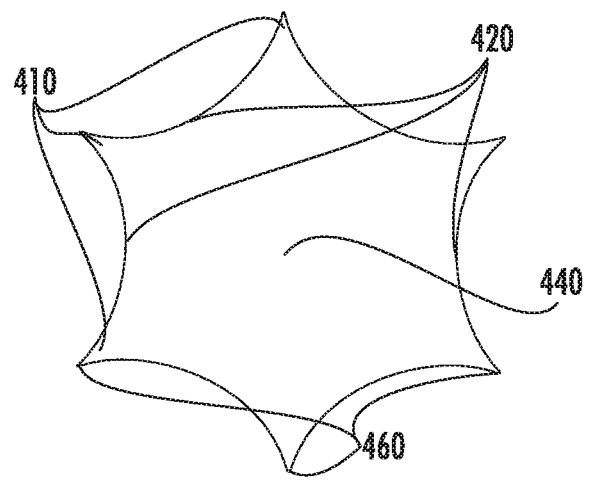
FIG. 25 is a cross-section view of the internal ultrasonic horn taken along line E-E of FIG. 22.
Figure 26:
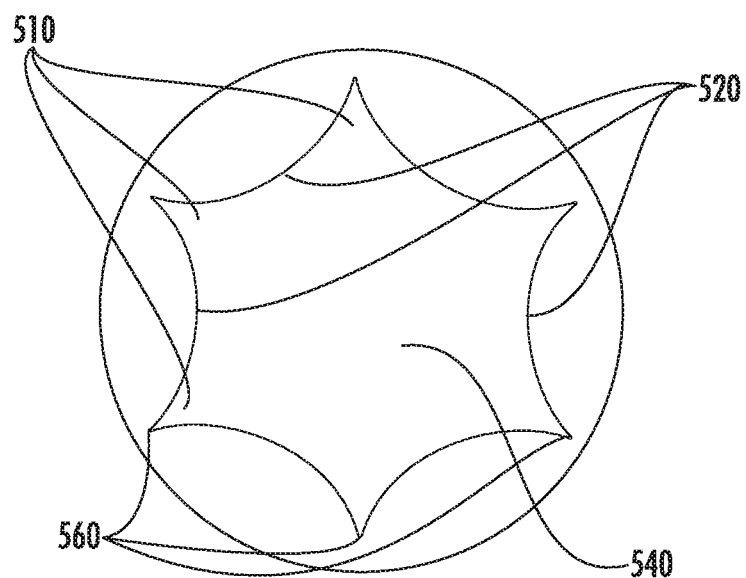
FIG. 26 is a cross-section view of the handpiece housing taken along line F-F of FIG. 23.
Figure 27:
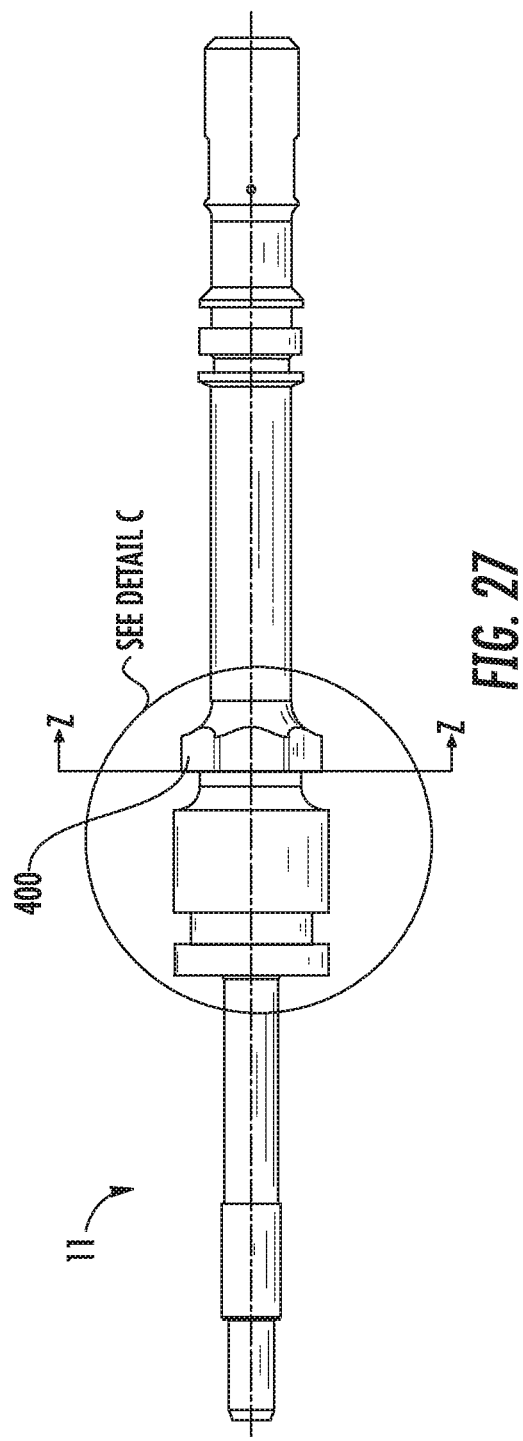
FIG. 27 is a side view of an internal ultrasonic horn.
Figure 28:
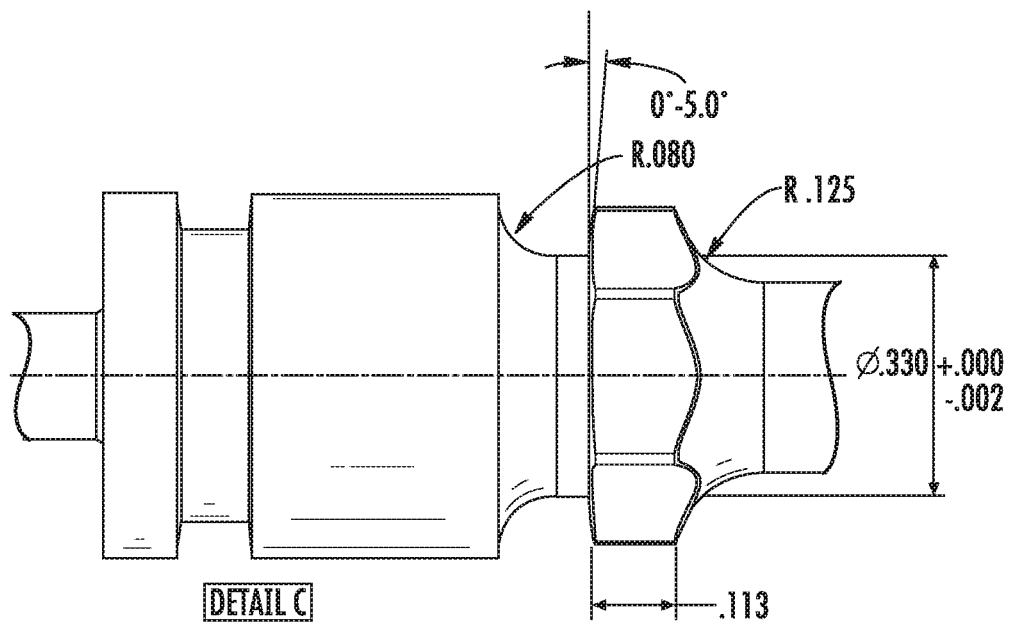
FIG. 28 is a detailed view of a section of the internal ultrasonic horn of FIG. 27.
Figure 29:
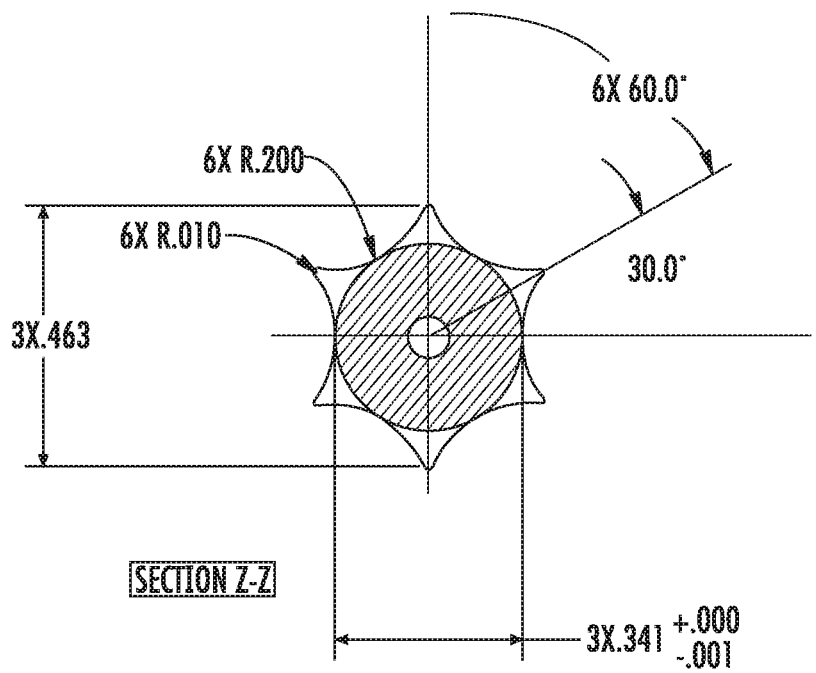
FIG. 29 is a cross-sectional view taken along line Z-Z of FIG. 27.
Figure 30:
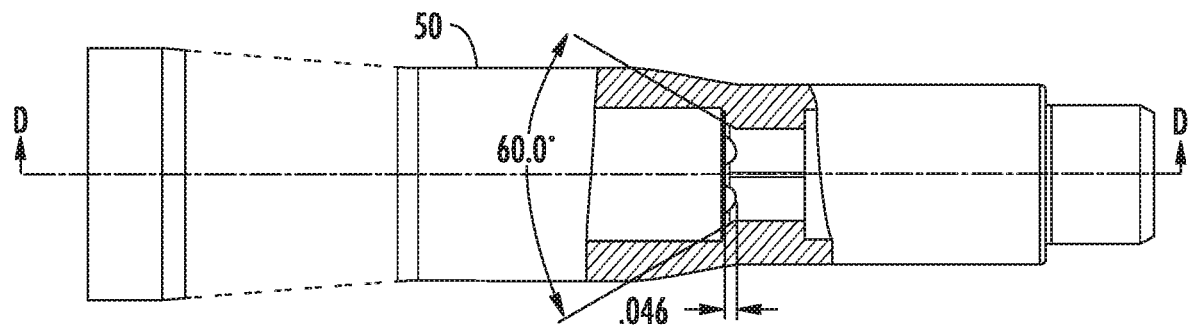
FIG. 30 is a cutaway illustration of a handpiece housing in accordance with embodiments of the present invention.
Figure 31:
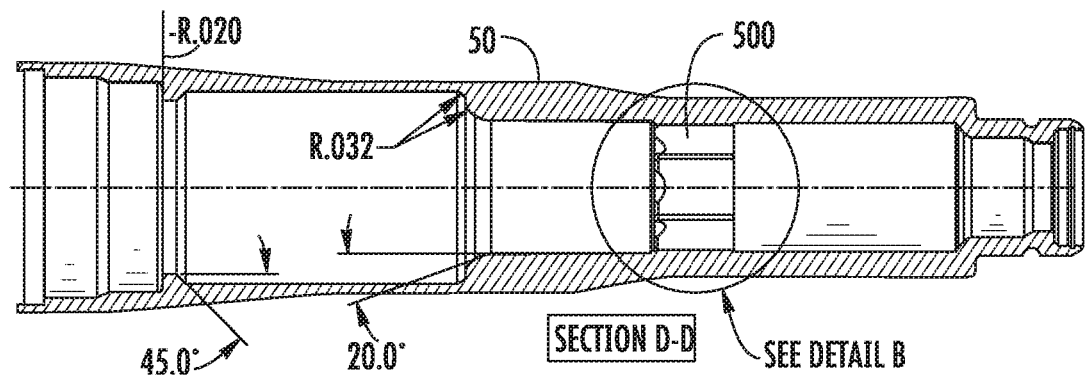
FIG. 31 is a cross-sectional view taken along line D-D of FIG. 30.
Figure 32:
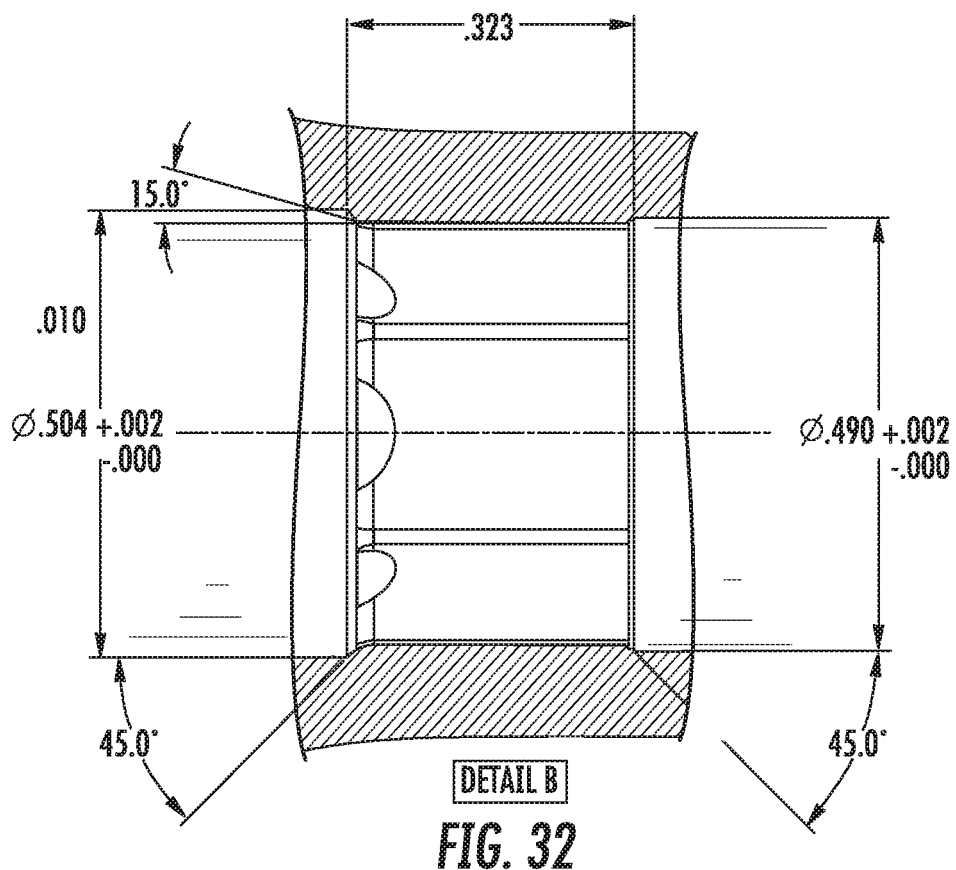
FIG. 32 is a detailed view of the housing engagement portion of the handpiece housing shown in FIG. 31.
Figure 33:
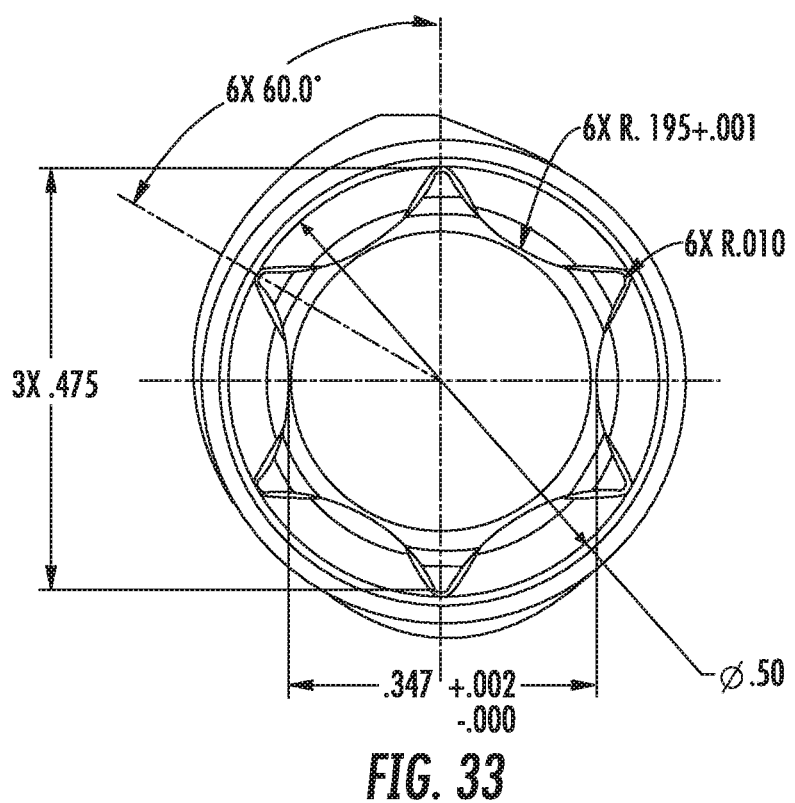
FIG. 33 is a cross-sectional view of the housing engagement portion shown in FIG. 32.

The benefit of the thermal diffuser is maintained at very high strokes for a handpiece and surgical tip combination, as exhibited with the electromechanical data and associated infrared thermal images at 5 minutes and 10 minutes of operation. High stroke and surgical tip and associated stack velocity at ultrasonic frequency are necessary to efficacy in tumor and tenacious tissue removal in neurosurgery and general surgery applications. The functionality of the thermal diffuser was also maintained at rated life use ratings, and as shown in the electromechanical data for a transducer tested to two twice life ratings. The transducer is a couple degrees above body temperature at twice rated life, although the stroke has increased marginally from initial calibration. The temperature at the case is more uniform and asymptotes with time, and is less objectionable to the acute tactile sensitivity of the surgeon. Some test data are shown in FIG. 19. The thermal diffuser can lower objectionable hot spots of over 55° C. to less than 41° C., and in most cases to about body temperature (37° C.), such that they are not felt by the surgeon.

In addition to incorporation of a thermal diffuser in some embodiments of the present invention, additional means may be taken to help reduce hot spots, for example, by eliminating interfaces that could cause heating under vibration of the stack. This may include removing any rigid epoxy from vibrating terminals. These terminals contact metallized electrodes on the piezoelectric ceramic disks. The terminals are vibrating at the high velocities associated with ultrasonic vibration and they are also thermally conductive, bringing the heat in the stack closer to the housing. Damping compounds that are rubber or rubber like may be placed on the terminals where they are soldered to flexible hook-up wires. Other means for reducing hot spots include using plasma metal coatings of minimal thickness, e.g. less than 25.4 micrometers of 0.001 inch.

Turning now to FIGS. 20 to 33, in accordance with other aspects of embodiments of the present invention, an ultrasonic surgical handpiece with an anti-rotation feature is provided. The anti-rotation feature reduces the risk of structural failure. The ultrasonic surgical handpiece 12 comprises an elongated housing 50 having an inner surface 550, a longitudinal axis L, and a housing engagement portion 500 on the inner surface 550. The housing engagement portion 500 has a transverse section that includes a central recess 540, six pointed recesses 510 pointing radially outward from the central recess and spaced evenly about the longitudinal axis L, and convex arcs 520 joining adjacent pointed recesses 510. The ultrasonic surgical handpiece 12 also comprises an internal ultrasonic horn 11 contained coaxially within the housing 50 and having an outer surface 450 and a horn engagement portion 400 on the outer surface 450. The horn engagement portion 400 has a transverse section that includes a central portion 440, six pointed protrusions 410 extending radially outward and spaced evenly about the longitudinal axis L, and concave arcs 420 joining adjacent pointed protrusions 410. Each of the pointed protrusions 410 corresponds in shape and size and is engageable with each of the pointed recesses 510. Each convex arc 520 has a side wall 530 which is parallel with the longitudinal axis L, and each concave arc 420 has a side wall 430 which is parallel with the longitudinal axis L.

Each convex arc is a section of a circle or some other curved shape, such as an ellipse. For example, each convex arc may be an arc of a circle having a radius in the range of about 0.05 to about 1.0 inch and preferably in the range of about 0.1 to about 0.5 inches. In an exemplary embodiment, each convex arc has a radius of about 0.2 inches. It is possible that the diameter or radius measurements of the plurality of convex arcs are not identical.

Likewise, each concave arc is a section of a circle or some other curved shape, such as an ellipse. For example, each concave arc may be an arc of a circle having a radius in the range of about 0.05 to about 1.0 inch and preferably in the range of about 0.1 to about 0.5 inches. In an exemplary embodiment, each convex arc has a radius of about 0.2 inches. It is possible that the diameter or radius measurements of the plurality of convex arcs are not identical, so long as the concave arcs correspond to and are engageable with the corresponding convex arcs.

At least one of the pointed recesses may have a recess tip portion that is rounded or curved or constitutes a portion of a sphere. The recess tip portion may have a radius in the range of about 0.005 to about 0.1 inches, for example, about 0.01 inches.

At least one of the pointed protrusions may have a protrusion tip portion that is rounded or curved or constitutes a portion of a sphere. The protrusion tip portion may have a radius in the range of about 0.005 to about 0.1 inches, for example, about 0.01 inches.

In an anti-rotation system in accordance with embodiments of the present invention, the housing engagement portion may comprise a plurality of pointed recesses, for example, at least 3 and preferably 5-7 pointed recesses, and the horn engagement portion may comprise a plurality of pointed protrusions, for example, at least 3 or preferably 5-7 pointed protrusions. The exemplary embodiment shown in the drawings has six pointed recesses in the cross-section of the housing engagement portion, and six pointed protrusions in the horn engagement portion. The horn engagement portion that has six pointed protrusions is referred to hereinafter as a "hexacog".

The hexacog design can be used for effective anti-rotation constraints. Unlike a hex nut, which can appear like an inclined plane with mechanical advantage in rotation, a cog presents a large surface area that resists rotation while distributing load and resultant stress. Inclined planes provide mechanical advantage for lifting the hex surface away from the mating feature or surface, causing cam-out. The mechanical advantage of an inclined plane is intuitive and employed in the earliest of human mechanisms, such as for lifting blocks of pyramids, zippers, and other simple but elegant mechanical systems.

Design of a metal to polymer interface should consider increasing area under greater loading such that the resistance to applied torque distributes and maintains stress under allowed limits. The stress in a simple hex is great, and increases with the mechanical advantage of the inclined plan of the hex, such that the area is reduced as load is applied. Polymers are forgiving relative to brittle materials in that local plastic deformation can occur conforming the polymer to the metal, rather than cracking under localized stress distribution. In the hexacog, as the 6 cog features cam-into the polymer, the load is distributed and the area opposing the applied torque becomes greater. The applied area divides the holding force by 6, and causes less stress concentration. In a cog design, often the material must fail for the mechanism to fail. The hexacog overcomes a failure mode of prior art handpieces, based on the cog railway anti-rotation mechanism. Known machining methods make the horn and housing mating geometries practical. The hexacog design was developed based on a fundamental understanding of the need to increase load distribution during elastic and local plastic deformation.

The greater the contact area, the less the stress for a given holding force or torque, such as determined by Hooke's Law, $\sigma$ (stress)=F (Force)/A (Area). It was determined that the cog feature could be introduced to a starting hex shape. A ball end-mill can be used to create the cog in the hex of the internal ultrasonic horn and a broach can be used to introduce the mating shape to the polymer housing. It was recognized that the cog mating features increased contact area under load, rather than allowing cam-out. Additionally, it was found in simulation that the cog mates with the six cogs of the housing, dividing maximum stress by a factor of 6 and multiplying allowed force for allowed stress by a factor of 6.

When the load due to tightening the surgical tip to the internal ultrasonic horn is removed, as it is in operation, the hexacog of the internal ultrasonic horn is free to vibrate or slide longitudinally and has only casual contact with the housing. The hexacog feature of the internal horn is also located close to a node, of minimum vibration, in the standing wave of the ultrasound.

If the flats 111 of the internal horn are not held during tightening of the surgical tip to high torque levels, the hexacog prevents rotation of the transducer in the polymer housing. In an exemplary embodiment for a 36 kHz transducer, the hexacog is machined in a high cyclic fatigue life 6AL 4V titanium material and the mating polymer is polyphenylsulfone (PPSU). It is understood by those skilled in the art that other electrically insulating polymers, such as polyetherimide plastic, can be utilized. The hexacog can be implemented for any ultrasonics frequency transducer, such as 23 kHz, 36 kHz, or 55 kHz transducer.

Other locations of the hexacog along the length of the internal horn and polymer case are possible, as well as other overall diameters and widths of the hexacog feature are within the scope of embodiments of the present invention.

Actual housings were ultimately tested to more than 600 fastening and loosening events of greater than necessary torque. Additionally, a handpiece was tested beyond rated torque events following more the 220 autoclaves, where weathering and embrittlement could occur. Given that the torque applied without use of the torque base has been accommodated to greater than 200 rated uses, there is a high degree of certainty that the failure mode of twisting the transducer in the housing has been eliminated. The hexacog enables in excess of 200 torque events at greater than rated torque, where previously even single or few errant events could cause failure.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The embodiments may be embodied in other forms without departure from the scope and essential characteristics thereof. The embodiments described therefore are to be considered in all respects as illustrative and not restrictive. Although the present invention has been described in terms of certain preferred embodiments, other embodiments that are apparent to those of ordinary skill in the art are also within the scope of the invention.

We claim:

1. A surgical handpiece, comprising:
   a housing;
   an electrical component within the housing;
   a thermal diffuser comprising a thermal conductive layer and an electrical insulating layer, wherein both the thermal conductive layer and the electrical insulating layer are disposed between the housing and the electrical component, wherein the thermal conductive layer is closer to the housing than the electrical insulating layer;
   wherein the thermal conductive layer includes two or more thermal conductive material pieces combining to form a first inner circumference and a first outer circumference, wherein each one of the two or more thermal conductive material pieces includes a length, an inner radius, and an outer radius; and
   wherein at least a portion of a circumference of the two or more thermal conductive material pieces includes an overlapping area therebetween.

2. The surgical handpiece of claim 1, wherein the housing has an elongated body and the thermal diffuser is in a cylindrical or partially cylindrical form that fits in the elongated body around the electrical component.

3. The surgical handpiece of claim 1, wherein the thermal conductive layer is made of a material selected from the group consisting of copper, aluminum, nickel, silver, gold and alloys thereof.

4. The surgical handpiece of claim 1, wherein the electrical insulating layer is made of a material selected from the group consisting of polytetrafluoroethylene, polycarbonate, polypropylene and combinations thereof.

5. The surgical handpiece of claim 1, wherein the thermal conductive layer and the electrical insulating layer are bonded with an adhesive.

6. The surgical handpiece of claim 1, wherein the housing is made of an electrical insulating material.

7. The surgical handpiece of claim 1, wherein the electrical component is an ultrasonically powered transducer.

8. A surgical handpiece, comprising:
   a housing having an elongated body along a longitudinal axis;
   an ultrasonically powered transducer positioned within the elongated body of the housing;
   a thermal diffuser comprising a thermal conductive layer and an electrical insulating layer, wherein both the thermal conductive layer and the electrical insulating layer are disposed between the elongated body of the housing and the transducer, wherein the thermal conductive layer is closer to the elongated body of the housing than the electrical insulating layer; and
   wherein both the thermal conductive layer and the electrical insulating layer of the thermal diffuser are disposed adjacent the elongated body of the housing and are radially spaced outwardly from the transducer;
   wherein the thermal conductive layer includes two or more thermal conductive material pieces combining to form a first inner circumference and a first outer circumference, wherein each one of the two or more thermal conductive material pieces includes a length, an inner radius, and an outer radius; and
   at least one of the two or more thermal conductive material pieces includes a second inner circumference and a second outer circumference and at least one of the two or more thermal conductive material pieces includes a third inner circumference and a third outer circumference, wherein at least a portion of the length of adjacent thermal conductive material pieces overlap the second inner circumference with the third outer circumference, and wherein the electrical insulating layer is disposed along the second inner circumference and the third inner circumference of the two or more thermal conductive material pieces forming the first inner circumference.

9. The surgical handpiece of claim 8, wherein the full length of the adjacent thermal conductive material pieces overlap.

10. The surgical handpiece of claim 8, wherein the second inner circumference abuts the third outer circumference of the overlapping adjacent thermal conductive material pieces.

11. The surgical handpiece of claim 8, wherein the thermal conductive layer is made of at least copper and the electrical insulating layer is made of at least polytetrafluoroethylene.

12. The surgical handpiece of claim 8, wherein the thermal conductive layer and the electrical insulating layer are bonded with an adhesive.

* * * * *